United States Patent

Ito et al.

Patent Number: 5,604,241
Date of Patent: Feb. 18, 1997

[54] SUBSTITUTED BENZYLAMINOQUINUCLIDINES AS SUBSTANCE P ANTAGONISTS

[75] Inventors: Fumitaka Ito, Chita-gun; Kunio Satake, Handa; Kaoru Shimada, Kariya, all of Japan

[73] Assignee: Pfizer Inc., New York, N.Y.

[21] Appl. No.: 416,913

[22] PCT Filed: Sep. 30, 1993

[86] PCT No.: PCT/US93/09168

§ 371 Date: Apr. 20, 1995

§ 102(e) Date: Apr. 20, 1995

[87] PCT Pub. No.: WO94/08997

PCT Pub. Date: Apr. 28, 1994

[30] Foreign Application Priority Data

Oct. 21, 1992 [JP] Japan .................... 4-283135

[51] Int. Cl.$^6$ .................. A61K 31/445; C07D 453/02
[52] U.S. Cl. .................. 514/305; 546/133
[58] Field of Search .................. 546/133; 514/305

[56] References Cited

U.S. PATENT DOCUMENTS 5,162,339  11/1992  Lowe, III ................ 514/305
5,288,730  2/1994  Baker ................ 514/305

OTHER PUBLICATIONS

Delgado, JN, Remers WA. "Textbook of Organic Medicinal and Pharmaceutical Chemistry" (1991) 9th Ed. p. 30.

Primary Examiner—C. Warren Ivy
Assistant Examiner—Evelyn Huang
Attorney, Agent, or Firm—Peter C. Richardson; Paul H. Ginsburg

[57] ABSTRACT

Compounds useful in the treatment of inflammatory disorders, central nervous system disorders and other disorders of the formula I

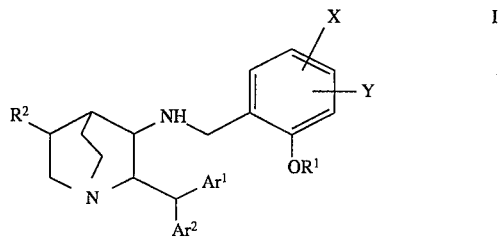

and the pharmaceutically-acceptable salts thereof, wherein $Ar^1$ and $Ar^2$ are each independently aryl or substituted aryl; $R^1$ is alkyl having from 1 to 6 carbon atoms;

$R^2$ is hydrogen or alkyl having from 1 to 6 carbon atoms;

and either X and Y are taken separately and they are each, independently, hydrogen, dialkylphosphoryl having 2 to carbon atoms, alkyl having from 1 to 6 carbon atoms, alkenyl having from 2 to 6 carbon atoms or alkynyl having from 2 to 6 carbon atoms; or X and Y are taken together and they represent a hydrocarbon chain having 3, 4, or 5 carbon atoms, optionally containing up to 2 double bonds and optionally having 1 or 2 substituents selected from oxo, hydroxy and alkyl having from 1 to 6 carbon atoms; or Y is methoxy when X is ethyl; provided that when X and Y are taken together they are attached to adjacent carbon atoms; and provided that if either X or Y is hydrogen, then the other one must be alkenyl or alkynyl; and provided that when Y is methoxy and X is ethyl, then Y is at the 4-position and X is at the 5-position, $Ar^1$ or $Ar^2$ must each be phenyl, $R^1$ is methyl and $R^2$ is hydrogen.

11 Claims, No Drawings

1

SUBSTITUTED BENZYLAMINOQUINUCLIDINES AS SUBSTANCE P ANTAGONISTS

This application is the national phase of PCT/US93/ 09168, filed on Sep. 30, 1993 and published as WO94/08997 on Apr. 28, 1994.

TECHNICAL FIELD

This invention relates to novel and useful substituted benzylaminoquinuclidine compounds of interest to those in the field of medical chemistry and chemotherapy. More particularly, it is concerned with a novel series of substituted 3-aminoquinuclidines, including their pharmaceutically acceptable salts, which are of special value in view of their ability to antagonize substance P. In this way, these compounds are of use in treating gastrointestinal disorders, central nervous system disorders, inflammatory diseases, asthma, pain and migraine. The invention also includes a new method of therapy within its scope.

BACKGROUND ART

E. J. Warawa in U.S. Pat. No. 3560510 discloses certain 3-amino-2-benzhydrylquinuclidines as being useful as diuretic agents, with the corresponding unsubstituted 3-benzylamino compounds acting as intermediates for same. Additionally, E. J. Warawa et al. in the *Journal of Medicinal Chemistry*, Vol.18, p.587 (1975) extends this work to other members of the series wherein the 3-amino moiety is either ethylamino, β-phenylethylamino, β-isopropylamino, or 2-furfurylamino, but in no instance is there any substitution on the phenyl group itself.

Furthermore, neither of the aforementioned documents teaches or suggests any of these compounds to be useful as substance P antagonists.

Substance P is a naturally occurring undecapeptide belonging to the tachykinin family of peptides, the latter being so-named because of their prompt stimulatory action on smooth muscle tissue. More specifically, substance P is a pharmaceutically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B. E. B. Sandberg et al., *Journal of Medicinal Chemistry*, Vol. 25, p.1009 (1982)), as well as in central nervous system disorders such as anxiety and schizophrenia, in respiratory and inflammatory diseases such as asthma and rheumatoid arthritis, respectively, and in gastrointestinal disorders and diseases of GI tract, like ulcerative colitis and Crohn's diseases, etc (see D. Regoli in "*Trends in Cluster Headache*" edited by F. Sicuteri et al., Elsevier Scientific Publishers, Amsterdam, 1987, PP. 85–95).

In the recent past, some attempts have been made to provide peptide-like substances that are antagonists for substance P and other tachykinin peptides in order to more effectively treat the various disorders and diseases listed above. The peptide-like nature of such substances makes them too labile from a metabolic point of view to serve as practical therapeutic agents in the treatment of disease. The non-peptidic antagonists of the present invention, on the other hand, do not possess this drawback, being far more stable from a metabolic point of view than the previously-discussed prior art agents.

Compounds of similar structure and similar pharmacological activity to the object compounds of the present invention, are described in WO 90/50729 and WO 92/20676.

Particularly, WO 90/05729 discloses a series of cis-3-[(cyclic)methylamino]-2-[(α-substituted)arylmethyl] quinuclidines including 2-benzhydryl derivatives, 2-substituted benzhydryl derivatives (wherein the substituents were alkyl, alkoxy, halogen and the like), 2-(bis-(2-thienyl)methyl) derivatives and the like. Furthermore, it shows that compounds disclosed in WO 90/05729 have activity as substance P antagonists, antiinflammatory activity and antipsychotic activity.

Under the circumstances, the present inventors have worked to prepare compounds useful as substance P antagonist, and after extensive research, have succeeded in synthesizing a series of compounds as will be disclosed in detail herein.

BRIEF DISCLOSURE OF THE INVENTION

The present invention provides novel disubstituted quinuclidine derivatives of the following chemical formula and the pharmaceutically acceptable salts thereof:

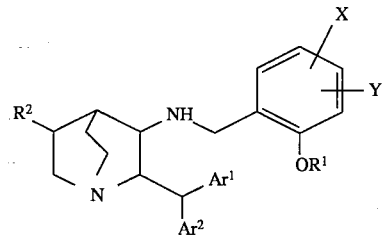

wherein $Ar^1$ and $Ar^2$ are each independently aryl or substituted aryl;

$R^1$ is alkyl having from 1 to 6 carbon atoms;

$R^2$ is hydrogen or alkyl having from 1 to 6 carbon atoms;

and either X and Y are taken separately and they are each, independently, hydrogen, dialkylphosphoryl having from 2 to 12 carbon atoms, alkyl having from 1 to 6 carbon atoms, alkenyl having from 2 to 6 carbon atoms or alkynyl having from 2 to 6 carbon atoms; or X and Y are taken together and they represent a hydrocarbon chain having 3, 4, or 5 carbon atoms, optionally containing up to 2 double bonds and optionally having 1 or 2 substituents selected from oxo, hydroxy and alkyl having from 1 to 6 carbon atoms, viz., and Y is at the 4-position and X is at the 5-position and $Ar^1$ and $Ar^2$ are both phenyl and $R^1$ is methyl and $R^2$ is hydrogen or Y is methoxy when X is ethyl;

provided that when X and Y are taken together they are attached to adjacent carbon atoms; and provided that if either X or Y is hydrogen, then the other one must be alkenyl or alkynyl.

The compounds of formula I show pharmaceutical activity as substance P antagonists. Therefore they are useful for treatment or prevention of a condition selected from the group consisting of inflammatory diseases (e.g., arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic disease such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human. Accordingly, the present invention includes pharmaceutical compositions for antagonizing mammal's Substance P which comprises a pharmaceutically acceptable carrier or diluent and a compound of formula I or a pharmaceutically acceptable salt thereof. These pharmaceutical compositions are useful for treating or preventing one of the aformentioned conditions, in a mammal, including a human.

The present invention also relates to a method of antagonizing substance P in a mammalian subject, which comprises administering to said subject an effective amount of a compound of formula I. In this way, the compounds of formula I are useful for treating or preventing the aforementioned conditions in a mammal, including a human.

DETAILED DISCLOSURE OF THE INVENTION

In this specification:

The term "alkyl" is used herein to mean straight or branched hydrocarbon chain radicals including, but not limited to, methyl, ethyl, n-propyl, isopropyl, n-butyl, isobutyl, t-butyl, and the like.

The term "alkenyl" is used herein to mean straight or branched hydrocarbon chain radicals having one double bond including, but not limited to, ethenyl, 1- and 2-propenyl, 2-methyl-l-propenyl, 1- and 2-butenyl and the like.

The term "alkynyl" is used herein to mean straight or branched hydrocarbon chain radicals having one triple bond including, but not limited to, ethynyl, propynyl, butynyl and the like.

The term "aryl" is used herein to mean aromatic radicals including, but not limited to, phenyl, naphthyl, pyridyl, quinolyl, thienyl, furyl, oxazolyl, tetrazolyl, thiazolyl, imidazolyl, pyrazolyl and the like. There may be mentioned alkyl, alkoxy, alkylthio, halogen, cyano, nitro, phenoxy, mono- or dialkylamino and the like as the substituents on the aryl.

The term "alkoxy" is used herein to mean —$OR^3$ ($R^3$ is alkyl) including, but not limited to, methoxy, ethoxy, propoxy, isopropoxy, n-butoxy, isobutoxy, t-butoxy and the like.

The term "halogen" is used herein to mean radicals derived from the elements fluorine, chlorine, bromine and iodine.

The term "alkylthio" is used herein to mean —$SR^4$ ($R^4$ is alkyl) including, but not limited to, methylthio, ethylthio, n-propylthio, isopropylthio, n-butylthio, isobutylthio, t-butylthio and the like.

The term "dialkylphosphoryl" is used herein to mean —$P(O)(OR^5)(OR^6)$ ($R^5$ and $R^6$ are alkyl) including, but not limited to, diethylphosphoryl, ethylmethylphosphoryl and the like.

The preferred groups for $Ar^1$ and $Ar^2$ are phenyl, thienyl, fluorophenyl, chlorophenyl and bromophenyl, especially phenyl. Especially preferred for $Ar^1$—CH—$Ar^2$ is diphenylmethyl.

A particularly preferred sub-group of compounds of the invention consists of the compounds of formula I, wherein $Ar^1$ and $Ar^2$ are each phenyl, $R^1$ is methyl, $R^2$ is hydrogen, X is alkenyl or alkynyl and Y is hydrogen.

Another preferred sub-group of compounds of the invention consists of the compounds of the formula I, wherein $Ar^1$ and $Ar^2$ are each phenyl, $R^1$ is methyl, $R^2$ is hydrogen and X and Y are each alkyl.

Yet another preferred sub-group of compounds of the invention consists of the compounds of the formula I, wherein $Ar^1$ and $Ar^2$ are each phenyl, $R^1$ is methyl, $R^2$ is hydrogen and X and Y represent $CH_2CH_2CH_2$ or $CH_2CH_2CH_2CH_2$.

Preferred individual compounds of this invention are the following:

(2S,3S)-N-(5-Isopropenyl-2-methoxyphenyl)methyl-2-diphenylmethyl-1-azabicyclo[2.2.2]octan-3-amine;

(2S,3S)-N-(2-Methoxy-5-vinylphenyl)methyl-2-diphenylmethyl-1-azabicyclo[2.2.2]octan-3-amine;

(2S,3S)-N-(2-Methoxy-4,5-dimethylphenyl)methyl-2-diphenylmethyl-1-azabicyclo[2.2.2]octan-3-amine;

(2S,3S)-N-(5,6,7,8-Tetrahydro-3-methoxy-2-naphthyl)methyl-2-diphenylmethyl-1-azabicyclo[2.2.2]octan-3-amine;

(2S,3S)-N-(5-Methoxyindan-6-yl)methyl-2-diphenylmethyl-1-azabicyclo[2.2.2]octan-3-amine;

(2S,3S)-3-(2,4-Dimethoxy-5-ethylbenzylamino)-2-diphenylmethyl-1-azabicyclo[2,2,2]octane; and (2S,3S)-2-Diphenylmethyl-N-[2-methoxy-5-(diethylphosphoryl)phenyl]methyl-1-azabicyclo[2.2.2]octan-3-amine.

The compounds of formula I may form acid addition salts. The pharmaceutically acceptable acid addition salts are those formed from acids which form non-toxic acid salts.

The novel compounds of the present invention can be prepared by the following methods.

The compounds of formula I may be prepared by a number of synthetic methods well known by those skilled in the art. See for instance, WO 90/05729. Thus, the following routes 1 and 2 (indicated as the following equations) are available to prepare the objective compounds of the present invention.

Equation 1

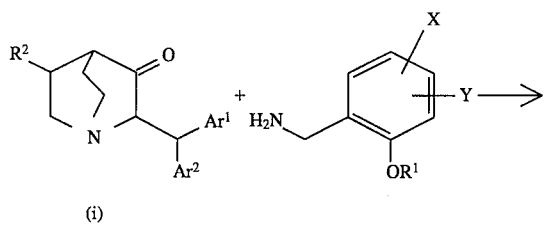

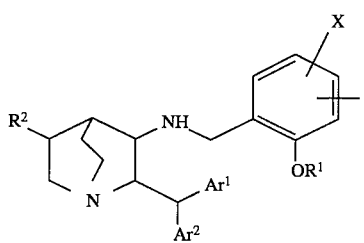

Equation 2

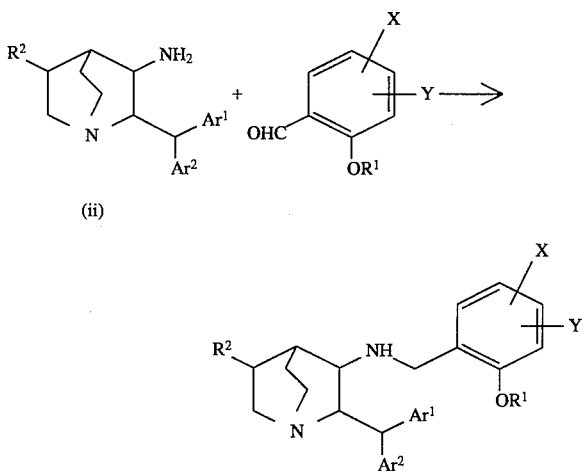

(wherein all the symbols are the same as in formula I).

The route in equation 1 is through the condensation of a 2-diarylmethylquinuclidine-3-one (i) and a substituted benzylamine, and subsequent reduction of a resulting intermediate, an imine.

The quinuclidin-3-one derivative (i) can be synthesized according to the similar manner with known methods [i.e., U.S. Pat. No. 3,560,510, Journal of the Chemical Society (London), P. 1241 (1939) and WO 90/05729].

The direct introduction of a benzylamino group at 3-position of the quinuclidin-3-one (i) is accomplished by, first, formation of an imine from (i) and the benzylamine, in most cases, catalyzed by acid (e.g. camphor sulfonic acid in hot toluene with azeotropic removal of water.

The reduction of C=N double bond in the imine can be completed by reaction with an appropriate hydrogen source. For example, catalytic hydrogenation or various reduction reagent such as aluminium reduction agents, boranes, borohydrides or trialkylsilanes are available. In most of the cases, the reaction with trialkylboranes (e.g. 9-BBN) or NaBH(OAc)$_3$ in THF or methylene chloride at room temperature for a half hour to a few days gives satisfactory results.

The substituted benzylamine used in equation 1 can be prepared from a following substituted benzaldehyde according to methods well known by those skilled in the art (i.e. reductive amination with ammonia).

The route in equation 2 is through the condensation of 3-amino-2-diarylmethylquinuclidine (ii) and a substituted benzaldehyde followed by reduction.

The 3-aminoquinuclidine derivative (ii) can be synthesized in a similar manner with *Journal of Medicinal Chemistry*, Vol. 18, p. 587 (1975).

In case of preparing the substituted benzaldehyde, the standard methods (formylation of a substituted alkoxybenzene) well known by those skilled in the art in the following literature can be used: (A) Duff's reaction (hexamethylenetetramine/TFA), Synth. Commun., 15, 61 (1985), (B) TiCl4/dichloromethylether, J. Org. Chem., 51, 4073 (1986), (C) A process by two step reaction (HCl, HCHO, then 2-nitropropane, NaOMe), JP-58-501127 and (D) J. Amer. Chem. Soc., 2466, (1955). Additionally, in order to prepare the substituted benzaldehyde, a Pd-catalyzed coupling reaction with halosubstituted alkoxybenzene in the following literature can be employed: (E) Angew. Chem. Int. Ed. Engl., 25, 508 (1986), J. K. Stille et al., (F) J. Org. Chem., 53 1170 (1988), J. K. Stille et al., (G) Tetrahedron Lett., 4467 (1975), K. Sonogashira et al., (H) Synthesis, 627 (1980), N. Hagihara et al.

In case of preparing 5-alkenyl-2-alkoxybenzaldehyde or 5-alkynyl-2-alkoxybenzaldehyde related to this invention, a corresponding alkenyltin compound or alkyne compound is reacted with 2-alkoxy-5-bromo (or iodo) benzaldehyde in a reaction inert solvent in the presence of a suitable Pd catalyst. Preferred Pd catalyst is Pd(PPh$_3$)$_4$ or PdCl$_2$(PPh$_3$)$_2$. Preferred range of temperature is from room temperature to the reflux temperature. Preferred reaction time is from 1 hr to 48 hr. Preferred solvent is selected from DMF, THF, toluene etc. for 5-alkenyl-2-alkoxybenzaldehyde or diethylamine, piperidine, triethylamine etc. for 5-alkynyl-2-alkoxybenzaldehyde.

In the reaction of equation 2, the direct arylmethylation is also possible by the reductive amination [e.g. sodium cyanoborohydride in methanol; the *Journal of American Chemical Society*, 93, 2897 (1971)].

When X forms a saturated or unsaturated carbon ring with Y, the compounds of present invention can be synthesized by using either route A or B.

Route A

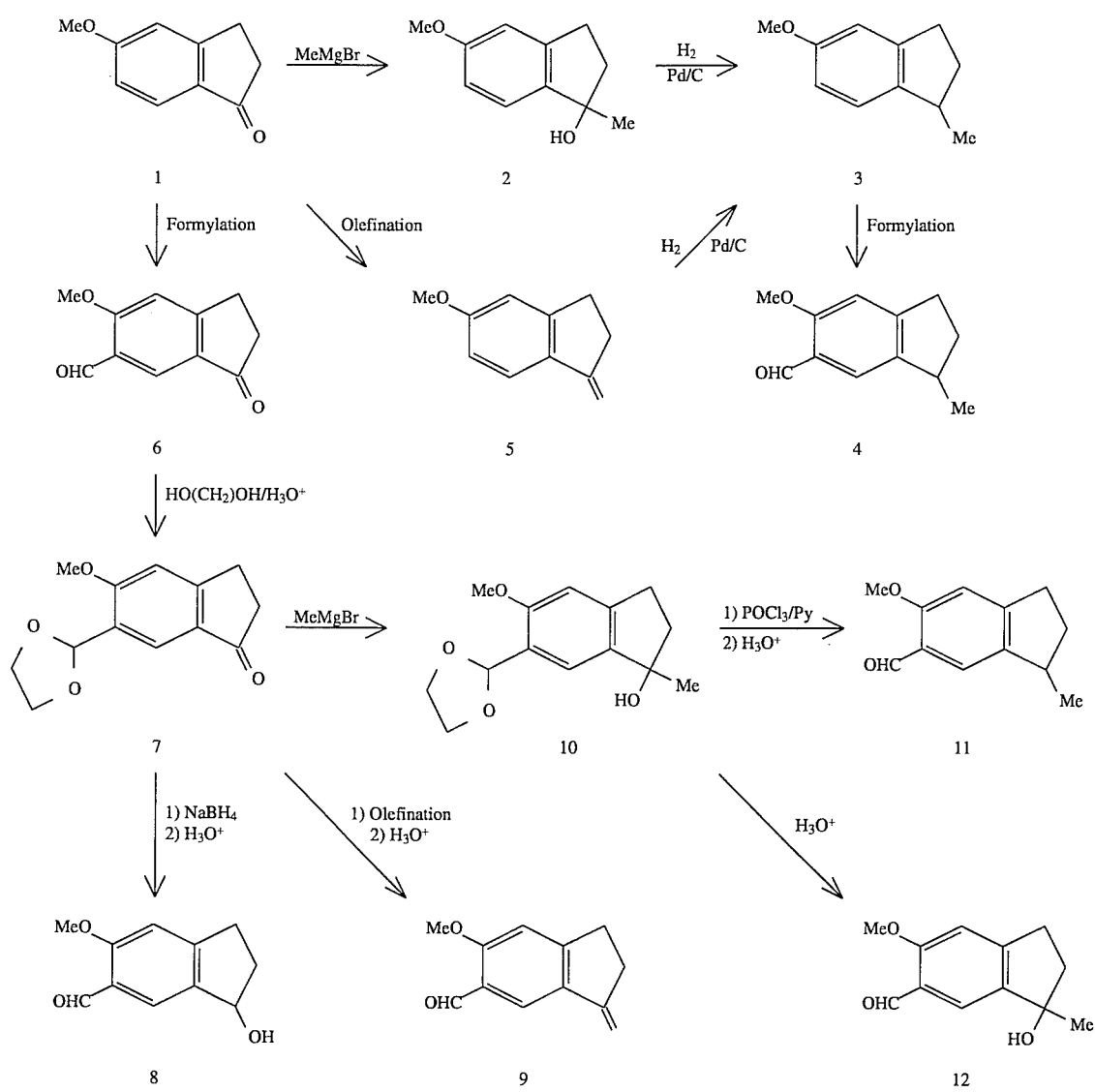

Route B

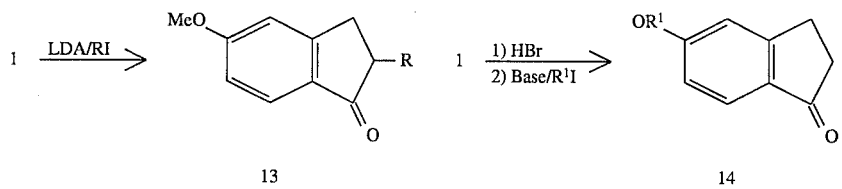

Thus the starting materials, aldehydes in equation 2 can be obtained by changing the substituents that are well-known method to those versed in the art. For example, various aldehydes can be synthesized by using synthetic route A from commercially available 5-methoxyindanone (1) as a starting material.

Thus, aldehydes (4) which is converted carbonyl to methyl in Formula (1) is obtained by formulating 5-methoxy-1-methylindan (3) which is generated by the Grignard reaction followed by hydrogenation. The various methods which mentioned above are adapted to this formulation reaction. Compound (3) is also obtained by olefination followed by reduction. In olefination e.g. Wittig reaction, Organic reaction, 14, 270 (1965) and Tebbe's reagent, Journal of the American Chemical Society, 111, 4392 (1989). On the other hand the direct formylation gives the aldehyde which has carbonyl group in the carbon ring.

The aldehyde (8) which converted from carbonyl of (6) to hydrogen is obtained by protecting (6) which is obtained by direct formylation of (1), $NaBH_4$ reduction followed by deprotection. The protecting group and its deprotection can be selected in what described in Protective Groups in Organic Synthesis written by T. W. Green and P.G.M. Wuts.

Compound (7) can be converted to aldehyde (9) which has exomethylene group by olefination followed by deprotection. Compound (7) can be also converted to aldehyde (11) which has double bond in the methylene ring by dehydrating Grignard product (10). Direct deprotection can give (12) which has hydroxy group and methyl group.

On the other hand, as shown in synthetic route B (1) can be converted (13) which has alkyl group at adjacent position of carboxylic acid by LDA/alkyl halide condition and converted to (14) by demethylation by such as HBr followed by realkylation. Further many objective aldehydes can be synthesized by using the compounds (13) and (14) thus obtained as a starting material.

In addition in Wittig reaction, olefination reaction and alkylation reaction, the benzaldehydes which have methylene group with a designed length can be synthesized by increasing or decreasing the carbon number of the reagent. These benzaldehydes can be used for the synthesis of the compounds of the present invention.

5-Methoxyindanone (1) which has three carbons in the methylene part are described as exemplified the starting material. 6-Methoxyindanon (commercially available) and methoxytetralons (which carbon number is four in methylene chain), needless to say, are adapted to the similar manner to the above.

The above objective compounds can be isolated and purified by conventional procedures, such as recrystallisation or chromatographic purification.

Inasmuch as the quinuclidine compounds of this invention all possess at least four asymmetric center, they are capable of occurring in various stereoisomeric forms or configurations. The present invention is meant to include all such forms within its scope. For instance, the diastereomeric mixtures can be separated by methods well known to those skilled in the art, e.g., by fractional crystallization and the like, while racemic mixtures can be separated by standard resolution methods of organic chemistry.

Insofar as the quinuclidine compounds of this invention are basic compounds, they are all capable of forming a wide variety of different salts with various inorganic and organic acids. Although such salts must be pharmaceutically acceptable for administration to animals, it is often desirable in practice to initially isolate the quinuclidine base compound from the reaction mixture as a pharmaceutically unacceptable salt and then simply convert to the free base compound by treatment with an alkaline reagent and thereafter, subsequently convert the free base to a pharmaceutically acceptable acid addition salt. The acid addition salts of the quinuclidine base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained.

The acid which are used to prepare the pharmaceutically acceptable acid addition salts of the aforementioned quinuclidine base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate))salts.

Some quinuclidine compounds of the invention which have also acidic groups are capable of forming base salts with various pharmaceutically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form nontoxic base salts with the herein described acidic quinuclidine derivatives. These particular non-toxic base salts include those derived form such pharmaceutically acceptable cations as sodium, potassium, calcium and magnesium, etc. These salts can easily be prepared by treating the aforementioned acidic quinuclidine compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The quinuclidine compounds of the formula I exhibit significant substance P receptor-binding activity and therefore, are of value in the treatment of a wide variety of clinical conditions which are characterized by the presence of an excess of said substance P activity. Such conditions include gastrointestinal disorders such as ulcer and colitis and other like diseases of the gastrointestinal tract, central nervous system disorders such as anxiety and psychosis, inflammatory diseases such as rheumatoid arthritis and inflammatory bowel diseases, respiratory diseases such as asthma, as well as pain in any of the aforesaid conditions, including migraine. Hence, these compounds are readily adapted to therapeutic use as substance P antagonists for the control and/or treatment of any of the aforesaid clinical conditions in mammals, including humans.

Some compounds of the present invention, when tested as an antiinflammatory agent, exhibit a significant degree of activity in the mustard oil-induced rat foot edema test [described by F. Lembeck et al., *British Journal of pharmacology*, Vol.105, P.527 (1992)].

The radiolabelled quinuclidine compounds of the formula I are useful as research and diagnostic tools in metabolism pharmacokinetic studies and in binding assays with the drug in both animal and human. Specific applications in research include radioligand binding assays, autoradiography studies and in vivo binding studies, while specific applications in the diagnostic area include studies of substance P receptor in the human brain, such as up/down regulation in a diseases state, and in vivo binding in the relevant tissues for inflammation, e.g., immune-type cell or cells that are directly involved in inflammatory bowel disorders and the like. Specifically, the radiolabelled forms of the quinuclidine compounds are the tritium and $^{14}$C-isotopes of substituted 3-aminoquinuclidine in this invention.

The quinuclidine compounds of formula I hereinbefore described can be administered to a mammalian subject, e.g., a human subject, via either the oral, parenteral or topical routes. In general, these compounds are most desirably administered to a human subject in doses ranging from about 1 mg to 300 mg per day, although variations will necessarily occur depending upon the weight and condition of the subject being treated and the particular route of administration chosen. However, a dosage level that is in the range of from about 0.06 mg to about 6 mg per kg of body weight per day is most desirably employed. Variations will occur depending upon the potency of the compound administered and the individual response of the human subject to said medicament, as well as the severity of the condition being treated, and the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day. The compounds of the present invention may be administered alone or in combination with pharmaceutically acceptable carriers or diluents by either of the three routes previously indicated, and such administration can be carried out in single or multiple doses. More particularly, the novel therapeutic agents of of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH)8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention, as substance P antagonists, is determined by their ability to inhibit the binding of substance P at its receptor sites in bovine caudate tissue or IM-9 cells employing radioactive ligands. The substance P antagonist activity of the herein described quinuclidine compounds is evaluated by using the standard assay procedure described by M. A. Cascieri et al., as reported in the *Journal of Biological Chemistry*, Vol.258, p.5158 (1983). This method essentially involves determining the concentration of the individual compound required to reduce by 50% the amount of radiolabelled substance P ligands at their receptor sites in said isolated cow tissues or IM-9 cells, thereby affording characteristic $IC_{50}$ values for each compound tested. In this test, some preferred compounds indicated low IC50 values of less than 0.1 nM with respect to inhibition of binding at its receptor.

The antiinflammatory activity of the compounds of the present invention is demonstrated in the previously mentioned mustard oil-induced rat foot edema test. In this test, antiinflammatory activity is determined as the percent inhibition of plasma protein extravasation in the hind paw of female Sprague-Dawley rats (weighing 100–150 g) in response to the application of mustard oil to the dorsal skin. The compounds of the present invention are dissolved in 0.1% methyl cellulose/water and dosed orally 1 h before mustard oil challenge. After Evans Blue injection solution (50 mg/kg, dissolved in saline including 0.02% bovine serum albumin)is injected intravenously, rat's hind paw is painted with 5% mustard oil in paraffin oil and 20 min later the foot is amputated, frozen, pulverized and the Evans Blue dye is extracted and determined colorimetrically.

Alternatively, the antiinflammatory activity of the compounds of the present invention is demonstrated by a capsaicin-induced plasma extravasation test. In this test, antiinflammatory activity is determined as the percent inhibition of plasma protein extravasation in the ureter of male Hartley guinea pigs (weighing 450–500 g) in response to the intraperitoneal injection of capsaicin into anesthetized animals. The compounds of the present invention are dissolved in 0.1% methyl cellulose/water and dosed orally 1 h before capsaicin challenge. Evans Blue dye (30 mg/kg) is administered intravenously 5 min before capsaicin challenge. The animals are killed 10 min after capsaicin injection and both right and left ureters are removed. The Evans Blue dye is extracted and determined colorimetrically.

In the above antiinflammatory tests, compounds are considered active if the difference in response between the drug-treated animals and a control group receiving the vehicle alone is statistically significant. In those test, some preferred compounds indicated high percentage with respect to inhibition of plasma protein extravasation.

The anti-psychotic activity of the compounds of the present invention as neuroleptic agents for the control of various psychotic disorders is determined primarily by a study of their ability to suppress substance P-induced hypermotility in rats. This study is carried out by first dosing the rats with a control compound or with an appropriate test compound of the present invention, then injecting the rats with substance P by intracerebral administration via canula and thereafter measuring their individual locomotor response to said stimuli.

EXAMPLES

The present invention is illustrated by the following examples. However, it should be understood that the invention is not limited to the specific details of these examples. Melting points were taken with a Yanako micro melting point apparatus and uncorrected. Infrared Ray absorption spectra (IR) were measured by a Shimazu infrared spectrometer (IR-470). Proton nuclear magnetic resonance spectra (NMR) were measured in CDCl$_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

EXAMPLE 1

(i)(2S,3S)-N-(5-Isopropenyl-2-methoxyphenylmethyl)-2-diphenylmethyl-1-azabicyclo[2.2.2]octan-3-amine-5-isopropenyl-o-anisaldehyde 5-Isopropenyl-o-anisaldehyde was prepared by J. K. Stille's method [*Journal of Organic Chemistry*, 52, 422 (1987)].

Tri-n-butyl-isopropenyltin (12.1 g, 36.6 mmol) dissolved in toluene (10 ml) was added to a mixture of 5-bromo-o-anisaldehyde (6.00 g, 27.9 mmol), tetrakis(triphenylphosphine)-palladium (1.21 g, 1.05 mmol), and 2,6-t-butyl-4-methylphenol (10 mg) in toluene (50 ml) under nitrogen at room temperature. This mixture was heated at reflux for 7 h. Ether and aq. KF solution (80 ml) were added to the reaction mixture, and the resulting solution was stirred for 3 h. Insoluble materials were removed by filtration through Celite. The filtrate was extracted with ether, and the organic phase was washed with 1N-NaHSO$_4$, aq. NaHCO$_3$ and brine. The extracts were dried over Na$_2$SO$_4$, and concentrated by evaporation. The residual oil was purified by chromatography (SiO$_2$, 140 g, 5% EtOAc-hexane) to afford -isopropenyl-o-anisaldehyde as a yellow oil (2.49 g, 51%). $^1$H NMR δ: 10.47 (s, 1H), 7.93 (d, J=2.6 Hz, 1H), 7.69 (dd, J=8.8, 2.6 Hz, 1H), 6.96 (d, J=8.8 Hz, 1H), 5.35 (br. s, 1H), 5.07 (m, 1H), 3.94 (s, 3H), 2.15 (m, 3H).

Tri-n-butyl-isopropenyltin was prepared according to D. Seyferth's method [*Journal of American Chemical Society*, 79, 515 (1957)].

(ii)(2S,3S)-N-(5-Isopropenyl-2-methoxyphenylmethyl)-2-diphenylmethyl-1-azabicyclo[2.2.2]octan-3-amine A mixture of 5-isopropenyl-o-anisaldehyde (717 mg, 4.07 mmol), (-)-(2S,3S)-cis-2-(diphenylmethyl)-1-azabicyclo [2.2.2]octane-3-amine(1.00g,3.42 mmol) and NaBH(OAc)$_3$ (1.01 g, 4.76 mmol) in CH$_2$Cl$_2$ was stirred at room temperature for 5 h. The reaction mixture was basified with K$_2$CO$_3$ aqueous solution (20 ml), extracted with CH$_2$Cl$_2$, dried over Na$_2$SO$_4$ and concentrated in vacuo. The residue was purified by chromatography (SiO$_2$, 2.0 g, 0–5%-MeOH /isopropylether) and recrystallized from isopropylether to afford the titled compound (820 mg, 53%). m.p.: 99.0°–103.0° C. IR (nujol): 1605, 1500, 1250, 1030 cm$^{-1}$ $^1$H NMR δ: 7.32–7.03 (m, 11H), 6.94 (d, J=2.2 Hz, 1H), 6.66 (d, J=8.5 Hz, 1H), 5.22 (m, 1H), 4.99 (m, 1H), 4.49 (d, J=12 Hz, 1H), 3.67 (dd, J=12, 8 Hz, 1H), 3.58 (d, =13 Hz, 1H), 3.54 (s, 3H), 3.20 (m, 1H), 3.18 (d, J=13 Hz, 1H), 2.93 (dd, J=8, 4 Hz, 1H), 2.75 (br. t, J=8 Hz, 2H), 2.60 (br. t, J=12 Hz, 1H), 2.14–2.04 (m, 1H), 2.10 (d, J=0.5 Hz, 3H), 1.98–1.85 (m, 1H), 1.72–1.45 (m, 2H), 1.26 (m, 2H).

EXAMPLE 2

(i)(2S,3S)-N-(2-Methoxy-5-vinylphenyl)methyl-2-diphenylmethyl-1-azabicyclo[2.2.2]octan-3-amine monomethanesulfonate 5-Vinyl-o-anisaldehyde was prepared by J. K. Stille's method [*Journal of Organic Chemistry*, 52, 420 (1987)] from 5-bromo-o-anisaldehyde and vinyltributyltin. $^1$H NMR δ: 10.46 (s, 1H), 7.88 (d, J=2.6 Hz, 1H), 7.60 (dd, J=9.0, 2.6 Hz, 1H), 6.97 (d, J=9.0 Hz, 1H), 6.67 (dd, J=17.6, 10.6 Hz, 1H), 5.70 (d, J=17.6 Hz, 1H), 5.12 J=10.6 Hz, 1H), 3.94 (s, 3H). (2S,3S)-N-(2-Methoxy-5-vinylbenzyl-2-diphenylmethyl-1-azabicyclo[2.2.2]octan-3-amine was prepared according to the procedure of Example 1 from 5-vinyl-o-anisaldehyde and (-)-(2S, 3S)-cis-2-diphenylmethyl-1-azabicyclo[2.2.2]octane-3-amine. The crude product was converted into monomethansulfonate by a conventional method and then the monomethansulfonate was recrystallized from acetone to afford the titled compound (0.45 g, 33.7%). m.p.: 225°–232° C. (acetone) IR (KBr):3410 (br.), 1502 (s), 1454 (m), 1300–1100 (br, m), 898 (s), 821 (s), 753 (s), 709 (s) cm$^{-1}$. $^1$H NMR δ:7.34–7.03(m,11H), 6.75 (d, J=2.0 Hz,1H), 6.66(d,=8.4 Hz, 1H), 6.59 (dd, J=17.8, 10.9 Hz, 1H), 5.55 (dd, J=17.8, 1.0 Hz, 1H), 5.12 (dd, J=10.9, 1.0 Hz, 1H 4.49 (d, J=12.4 Hz, 1H), 3.68 (dd, J=12.4, 8.0 Hz, 1H), 3.57 (d, J=13.0 Hz, 1H), 3.56 (s, 3H), 3.22 (d, J=13.0 Hz, 1H), 3.29–3.15 (m, 1H), 2.92 (dd, J=8.0, 4.0 Hz, 1H), 2.76 (m,2H), 2.60 (m,1H), 2.09 (m, 1H), 1.93 (m, 1H), 1.7–1.46 (m, 2H), 1.32–1.21 (m, 1H).

EXAMPLE 3

(i)(2S,3S)-N-(2-methoxy-4,5-dimethylphenyl)methyl-2-diphenylmethyl-1-azabicyclo[2.2.2]octan-3-amine dihydrochloride Preparation of 2-methoxy-4,5-dimethylbenzaldehyde This compound was synthesized according to the literature described in the general synthesis of this specification. $^1$H NMR δ: 10.38 (1H, s), 7.58 (1H, s), 6.77 (1H, s), 3.89 (3H, s), 2.31 (3H, s) and 2.21 (3H, s).

Preparation of (2S,3S)-N-(2-methoxy-4,5-dimethylphenyl)methyl-2-diphenylmethyl-1-azabicyclo [2.2.2]octan-3-amine dihydrochloride A mixture of 2-methoxy-4,5-dimethylbenzaldehyde (0.26 g, 1.57 mmol), (-)-(2S,3S)-cis-2-(diphenylmethyl)-1-aza bicyclo[2.2.2]octane-3-amine (0.40 g, 1.57 mmol) and NaBH(OAc)$_3$ (0.41 g, 1.92 mmol) in CH$_2$Cl$_2$ was stirred at room temperature for 5 h. The reaction mixture was washed with brine. CH$_2$Cl$_2$ layer was dried over Na$_2$SO$_4$ and concentrated in vacuo. The residue was recrystallized from ethanol to afford the titled compound (0.40 g). mp: 218°–225 ° C. IR (KBr): 3400, 3200, 1620, 1510 and 1455 cm$^{-1}$ $^1$H NMR (free base) δ:7.36–7.00 (10H, m), 6.51 (1H, s), 6.34 (1H, s), 4.48 (1H, d, J=12.1 Hz), 3.63 (1H, dd, J=12.1, 8.4 Hz), 3.52 (3H, s), 3.50 (1H, d, J=12.8 Hz), (1H, d, J=12.8 Hz), 2.90 (1H, dd, J=8.4, 4.0 Hz), 2.81–2.73 (2H, m), 2.66–2.55 (1H m), 2.20 (3H, s), 2.11 (3H, s), 2.10–2.04 (1H, m), 2.00–1.85 (1H, m), 1.65–1.45 (3H, m) and 1.30–1.18 (1H, m).

EXAMPLE 4

(2S,3S)-N-(5,6,7,8-Tetrahydro-3-methoxy-2-naphthyl)methyl-2-diphenylmethyl-1-azabicyclo[2.2.2]octan-3-amine To a solution of (-)-(2S,3S)-cis-2-diphenylmethyl-1-azabicyclo[2.2.2]octane-3amine (1.170 g, 4 mmol), 3-methyl-5,6,7,8-tetrahydro-2-naphthaldehyde (0.913 g, 4.8 mmol) and NaBH(OAc)$_3$ (0.933 g, 4.4 mmol) in CH$_2$Cl$_2$ was stirred at room temperture. The reaction mixture was basified with saturated NaHCO$_3$ solution (20 ml). CH$_2$Cl$_2$ layer was washed with water, dried over Na$_2$SO$_4$ and concentrated. The resulting residue was chromatographed on a silica gel column. The product was converted to the HCl salt by HCl-Ether (1.796 g). mp: 231° C. IR (KBr): 3420, 2900, 1620, 1505, 1445, 1260, 1105, 750 and 710 cm$^{-1}$ $^1$H NMR (free base) δ: 8.40 (1H, br), 7.92 (2H, m), 7.67 (2H, m), 7.43–7.18 (6H, m), 6.73 (1 H, m), 6.42 (1H, m), 6.10 (1H, m), 5.57 (1 H, d, J=12.5Hz), 5.53 (1H, m), 4.48 ) (1H, m), 4.34 (1 H, m), 4.16 (1 H, m), 3.83 (2H, m), 3.71–3.42 (4H, m), 3.31 (3H, s), 3.29 (2H, m), 2.77 –2.56 (5H, m), 2.40–1.95 (4H, m) and 1.78 (4H, m).

EXAMPLE 5

(2S,3S)-N-(5-Methoxyindan-6-yl)methyl-2-diphenyl-methyl-1-azabicyclo[2.2.2]octan-3--amine dihydrochloride This compound was prepared according to the similar manner with example 2. mp: 160°–163° C. IR (KBr): 3420, 1495 and 1460 cm$^{-1}$ $^1$H NMR (free base) δ:7.41–7.12 (9H, m), 7.12–7.02 (1H, m), 6.61 (1H, s), 6,37 (1H, s), 4.50 (1H, d, J=12.1 Hz), 3.66 (1H, dd, J=12.1, 7.7 Hz), 3.60–3.48 (1H, m), 3.54 (3H, s), 3.26 (1H, d, J=13.2 Hz), 3.28–3.15 (1H, m), 2.97–2.70 (7H, m), 2.81–2.73 (2H, m), 2.60 (1H, t, J=11.0 Hz), 2.14–1.87 (4H, m), 1.73–1.44 (2H, m) and 1.35–1.20 (1H, m).

EXAMPLE 6

(2S,3S)-3-(2,4-Dimethoxy-5-ethylbenzylamino)-2-diphenylmethyl-1--azabicyclo[2,2,2]octane monomesylate (i) 5-Ethyl-4-methoxy-o-anisaldehyde To a solution of hexamethylenetetramine (HMTA)(6.75 g, 48.1 mmol) in trifluoroacetic acid (TFA)(40 ml) heated at reflux was added a solution of 4-ethoxy-1,3-dimethoxybenzene, (4.0 g, 24.1 mmol) in TFA (40 ml) dropwise over 90 min. The reaction mixture was heated at reflux for 2 h. The dark solution was concentrated in vacuo with mild heating leaving a dark red syrup. Ice water was added to the syrup until it became cloudy, then stirred at room temperature for 20 min. The mixture was basified with solid K$_2$CO$_3$, then stirred at room temperature for 20 min, and extracted with CH$_2$Cl$_2$ (200 ml×4). The combined CH$_2$Cl$_2$ solution was washed with water and brine, dried over MgSO$_4$, and concentrated in vacuo to give a crude title compound (4.46 g) as a orange solid. The crude product was recrystallized from hexane-ethyl acetate to give title compound (2.51 g, 53.7%) as a pale yellow solid. $^1$H-NMR δ: 10.30 (s, 1H), 7.63 (s, 1H), 6.40 (s, 1H), 3.93 (s, 3H), 3.92 (s, 3H), 2.56 (q, J=7.3 Hz, 2H), 1.16 (t, J=7.3 Hz, 3H) IR(KBr, cm$^{-1}$): 1662, 1610, 1578, 1505, 1488, 1477, 1457, 1437, 1408, 1354, 1320, 1279, 1261, 1216, 1189, 1111, 1025, 908, 825, 697.

(ii) (2S,3S)-3-(2,4-Dimethoxy-5-ethylbenzylamino)-2-diphenylmethyl-1-azabicyclo[2,2,2]octane monomesylate This compound was prepared according to the similar manner with example 2. mp :222°–223° C. $^1$H NMR (free amine) δ: 7.39–7.02 (m, 10H), 6.39 (s, 1H), 6.29 (s, 1H), 4.50 (d, J=12.5 Hz, 1H), 3.80 (s, 3H), 3.70 (dd, J=7.7, 12.5 Hz, 1H), 3.56 (s, 3H), 360–3.47 (m, H), 3.31–3.08 (m, 1H), 3.15 (d, J=12.5 Hz, 1H), 2.92 (dd, J=4.0, 7.7 Hz, 1H), 2.86–2.40 (m, 5H), 2.16–1.87 (m, 2H), 1.74–1.43 (m, 2H), 1.36–1.18 (m, 1H), 1.12 (t, J=7.3 Hz, 3H). IR(KBr)(free amine): 3435, 3340, 1615, 1590, 1503, 1464, 1449, 1438, 1294, 1203, 117, 1037, 81 8, 798, 743, 701 cm$^{-1}$.

EXAMPLE 7

(2S,3S)-2-Diphenylmethyl-N-[2-methoxy-5-(diethylphosphoryl)phenyl]methyl-1-azabicyclo[2.2.2]octan-3-amine (i) 5-Diethylphosphoryl-2-methoxybenzaldehyde A mixture of 5-bromo-o-anisaldehyde (860 mg, 4.00 mmol), tetrakis(triphenylphosphine)palladium (0) (462 mg, 0.399 mmol), diethyl phosphite (607 mg, 4.40 mmol), triethylamine (1.10 ml, 7.94 mmol) was heated at 100° C. for 1 day. The reaction mixture was dissolved in methylene chloride, and washed with aq. sodium bicarbonate. The organic layer was dried over magnesium sulfate, and concentrated by evaporation.

The residue was purified by chromatography (silica-gel, 30% toluene/ethyl acetate) to afford 162 mg of title compound. $^1$H NMR δ: 10.46 (d, J=2.2 Hz, 1H), 8.23 (dd, J=13, 2 Hz, 1H), 8.04 (ddd, J=13, 9, 2 Hz, 1H), 7.09 (dd, J=9, 3 Hz, 1H), 4.00 (s, 3H). This material contained other impurities detected by $^1$H NMR.

(ii) (2S,3S)-2-DiphenylmethyI-N-[2-methoxy-5-(diethylphosphoryl)phenyl]methyl-1-azabicyclo[2.2.2]octan-3-amine Sodium triacetoxyborohydride (202 mg, 0.95 mmol) was added to a solution of (2S,3S)-2-diphenylmethyl-1-azabicyclo[2.2.2]octan-3-amine (150 mg, 0.51 mmol) and 5-diethylphosphoryl-2-methoxybenzaldehyde (150 mg, 0.55 mmol) dissolved in methylene chloride (5 ml) at rt, and the resulting solution was stirred for 16 h. Ethylene chloride and 1N sodium bisulfate were added to the reaction mixture. After 5 min the organic layer was washed with aq. sodium bicarbonate solution and brine. The extracts were dried over magnesium sulfate, and concentrated by evaporation. The residual oil was purified by following process: (1) silica-gel chromatography (4–14% methanol-methylene chloride), (2) Merck Lobar Li Chroprep NH2 (25–70%), (3) crystallization from diisopropyl ether. The title compound was obtained in a pure form (11 mg). IR (CH$_2$Cl$_2$) 1270 cm$^{-1}$ $^1$H NMR δ: 7.66 (ddd, J=13, 8, 2 Hz, 1H), 7.39 (dd, J=13, 2 Hz, 1H), 7.31–7.03 (m, 10H), 6.75 (dd, J=8, 3.5 Hz, 1H), 4.47 (d, 12.2 Hz, 1H), 4.10 (m, 4H), 3.69–3.57 (m, 2H), 3.54 (s, 3H), 3.25–3.10 (m, 1H), 3.19 (d, J=13 Hz, 1H), 1H), 2.87 (dd Hz, 1H), 2.75 (m, 2H), 2.60 (m, 1H), 2.05 (m, 1H), 1.88 (m, 1H), 1.70–1.20 (m, 3H), 1.35 (t, J=7 Hz, 3H), 1.34 (t, J=7 Hz, 3H).

We claim:

1. A compound of the following chemical formula or a pharmaceutically acceptable salt thereof:

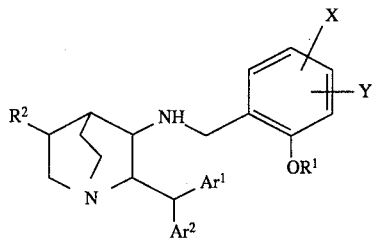

wherein Ar¹ and Ar² are each independently aryl or substituted aryl;

R¹ is alkyl having from 1 to 6 carbon atoms;

R² is hydrogen or alkyl having from 1 to 6 carbon and either X and Y are taken separately and they are each, independently, hydrogen, dialkylphosphoryl having 2 to 12 carbon atoms, alkyl having from 1 to 6 carbon atoms, alkenyl having from 2 to 6 carbon atoms; or X and Y are taken together and they represent a hydrocarbon chain having 3, 4, or 5 carbon atoms, optionally containing up to 2 double bonds and optionally having 1 to 2 substituents selected from oxo, hydroxy and alkyl having from 1 to 6 carbon atoms; or Y is methoxy when X is ethyl and Y is at the 4-position and X is at the 5-position and Ar¹ Ar² are both phenyl and R¹ is methyl and R² hydrogen;

provided that when X and Y are taken together they are attached to adjacent carbon atoms; and provided that if either X or Y is hydrogen, then the other one must be alkenyl or alkynyl.

2. A compound according to claim 1, wherein Ar¹ and Ar² are each phenyl, thienyl, fluorophenyl, chlorophenyl or bromophenyl.

3. A compound according to claim 2, wherein Ar¹ and Ar² are each phenyl, R¹ is methyl and R² is hydrogen.

4. A compound according to claim 3, wherein X is said alkenyl or said alkynyl and Y is hydrogen.

5. A compound according to claim 3, wherein X and Y are each said alkyl.

6. A compound according to claim 3, wherein X and Y are taken together and they represent $CH_2CH_2CH_2$ or $CH_2CH_2CH_2CH_2$.

7. A compound selected from the following:

(2S,3S)-N-(5-Isopropenyl-2-methoxyphenyl)methyl-2-diphenylmethyl-1-azabicyclo[2.2.2]octan-3-amine;

(2S,3S)-N-(2-Methoxy-5-vinylphenyl)methyl-2-diphenylmethyl-1-azabicyclo[2.2.2octan-3-amine;

(2S,3S)-N-(2-Methoxy-4,5-dimethylphenyl)methyl-2-diphenylmethyl-1-azabicyclo[2.2.2]octan-3-amine;

(2S,3S)-N-(5,6,7,8-Tetrahydro-3-methoxy-2-naphthylmethyl-2-diphenylmethyl-1-azabicyclo[2.2.2]octan-3-amine;

(2S,3S)-N-(5-Methoxyindan-6-yl)methyl-2-diphenylmethyl-1-azabicyclo[2.2.2]octan-3-amine;

(2S,3S)-3-(2,4-Dimethoxy-5-ethylbenzylamino)-2-diphenylmethyl-1-azabicyclo[2,2,2]octane; and (2S,3S)-2-Diphenylmethyl-N-[2-methoxy-5-(diethylphosphoryl)phenyl]methyl-1-azabicyclo[2.2.2]octan-3-amine.

8. A method for antagonizing substance P in a mammalian subject, which comprises administering to the said subject an effective amount of a compound of claim 1.

9. A method of treating a gastrointestinal or central nervous system disorders and the alleviation of inflammatory disease, asthma, pain or migraine in a mammalian subject, which comprises administerint to said subject a therapeutically effective amount of a compound of claim 1.

10. A pharmaceutical composition for antagonizing substance P in a mammalian subject which comprises a therapeutically effective amount of a compound of claim (1) or its pharmaceutically acceptable salt together with a pharmaceutically acceptable carrier.

11. A pharmaceutical composition for the treatment of gastrointestinal or central nervous system disorders and the alleviation of inflammatory disease, asthma, pain or migraine in a mammalian subject which comprises a therapeutically effective amount of a compound of claim (1) or its pharmaceutically acceptable salt together with a pharmaceutically acceptable carrier.

* * * * *